United States Patent [19]

Sherts

[11] Patent Number: 5,645,552
[45] Date of Patent: Jul. 8, 1997

[54] SURGICAL APPARATUS FOR SUTURING BODY TISSUE

[75] Inventor: Charles R. Sherts, Southport, Conn.

[73] Assignee: United States Surgical Corporation, Norwalk, Conn.

[21] Appl. No.: 371,200

[22] Filed: Jan. 11, 1995

[51] Int. Cl.$^6$ .................................................. A61B 17/04
[52] U.S. Cl. ............................ 606/145; 606/139; 606/147
[58] Field of Search .................................... 606/139, 144, 606/145, 146, 147, 148, 151, 157, 205

[56] References Cited

U.S. PATENT DOCUMENTS

| | | |
|---|---|---|
| 1,037,864 | 9/1912 | Saxton . |
| 1,131,163 | 3/1915 | Steedman . |
| 1,293,565 | 2/1919 | Smit . |
| 1,449,087 | 3/1923 | Bugbee . |
| 1,876,792 | 6/1932 | Thompson . |
| 2,213,830 | 9/1940 | Anastasi . |
| 2,434,133 | 1/1948 | Volk ........................................ 505/145 |

(List continued on next page.)

FOREIGN PATENT DOCUMENTS

| | | |
|---|---|---|
| 0482881 | 4/1992 | European Pat. Off. . |
| 0601676A2 | 6/1994 | European Pat. Off. . |
| 337579 | 9/1904 | France . |
| 9109097 | 10/1991 | Germany . |
| 4124383C1 | 5/1992 | Germany . |
| 4124381C1 | 8/1992 | Germany . |
| 4127812 | 2/1993 | Germany . |
| 4139628C1 | 3/1993 | Germany . |
| 1103-854 | 7/1984 | U.S.S.R. . |
| 1505-514 | 9/1989 | U.S.S.R. . |
| 1725847-A1 | 4/1992 | U.S.S.R. . |
| 1249853 | 10/1971 | United Kingdom . |
| 2260704 | 4/1993 | United Kingdom . |
| WO93/01750 | 2/1993 | WIPO . |

OTHER PUBLICATIONS

Aesculap Catalog, p. 401 (Date: 1905).

*Primary Examiner*—Michael Buiz
*Assistant Examiner*—Patrick W. Rasche

[57] ABSTRACT

A surgical apparatus for suturing body tissue comprising first and second jaws relatively movable between an open and closed position, a first needle retaining section having a first securing mechanism mounted therein removably mounted to the first jaw, and a second needle retaining section having a second securing mechanism mounted therein removably mounted to the second jaw. The surgical needle is transferable between the first and second sections upon closing of the jaws such that the surgical needle can be retained in either of the first and second sections by the respective securing mechanism.

29 Claims, 10 Drawing Sheets

U.S. PATENT DOCUMENTS

| | | |
|---|---|---|
| 2,880,728 | 4/1959 | Rights . |
| 3,090,386 | 5/1963 | Curtis . |
| 3,349,772 | 10/1967 | Rygg . |
| 3,470,875 | 10/1969 | Johnson . |
| 3,807,407 | 4/1974 | Schweizer . |
| 3,842,840 | 10/1974 | Schweizer . |
| 3,901,244 | 8/1975 | Schweizer . |
| 3,946,740 | 3/1976 | Bassett . |
| 4,021,896 | 5/1977 | Stierlein . |
| 4,109,658 | 8/1978 | Hughes ................................. 606/145 |
| 4,161,951 | 7/1979 | Scanlan, Jr. . |
| 4,164,225 | 8/1979 | Johnson et al. . |
| 4,236,470 | 12/1980 | Stenson . |
| 4,345,601 | 8/1982 | Fukuda . |
| 4,373,530 | 2/1983 | Kilejian . |
| 4,471,781 | 9/1984 | Di Giovanni et al. . |
| 4,491,135 | 1/1985 | Klein . |
| 4,580,567 | 4/1986 | Schweitzer et al. . |
| 4,621,640 | 11/1986 | Mulhollan et al. . |
| 4,635,638 | 1/1987 | Weintraub et al. . |
| 4,890,615 | 1/1990 | Caspari et a l. . |
| 4,923,461 | 5/1990 | Caspari et al. . |
| 4,935,027 | 6/1990 | Yoon . |
| 4,957,498 | 9/1990 | Caspari et al. . |
| 5,059,201 | 10/1991 | Asnis . |
| 5,100,421 | 3/1992 | Christoudias . |
| 5,171,257 | 12/1992 | Ferzli . |
| 5,188,636 | 2/1993 | Fedotov . |
| 5,207,693 | 5/1993 | Phillips . |
| 5,217,471 | 6/1993 | Burkhart . |
| 5,224,948 | 7/1993 | Abe et al. . |
| 5,242,458 | 9/1993 | Bendel et al. . |
| 5,254,126 | 10/1993 | Filipi et al. . |
| 5,261,917 | 11/1993 | Hasson et al. . |
| 5,281,220 | 1/1994 | Blake, III ................................. 606/46 |
| 5,336,191 | 8/1994 | Davis et al. ............................ 604/165 |
| 5,474,568 | 12/1995 | Scott ....................................... 606/139 |

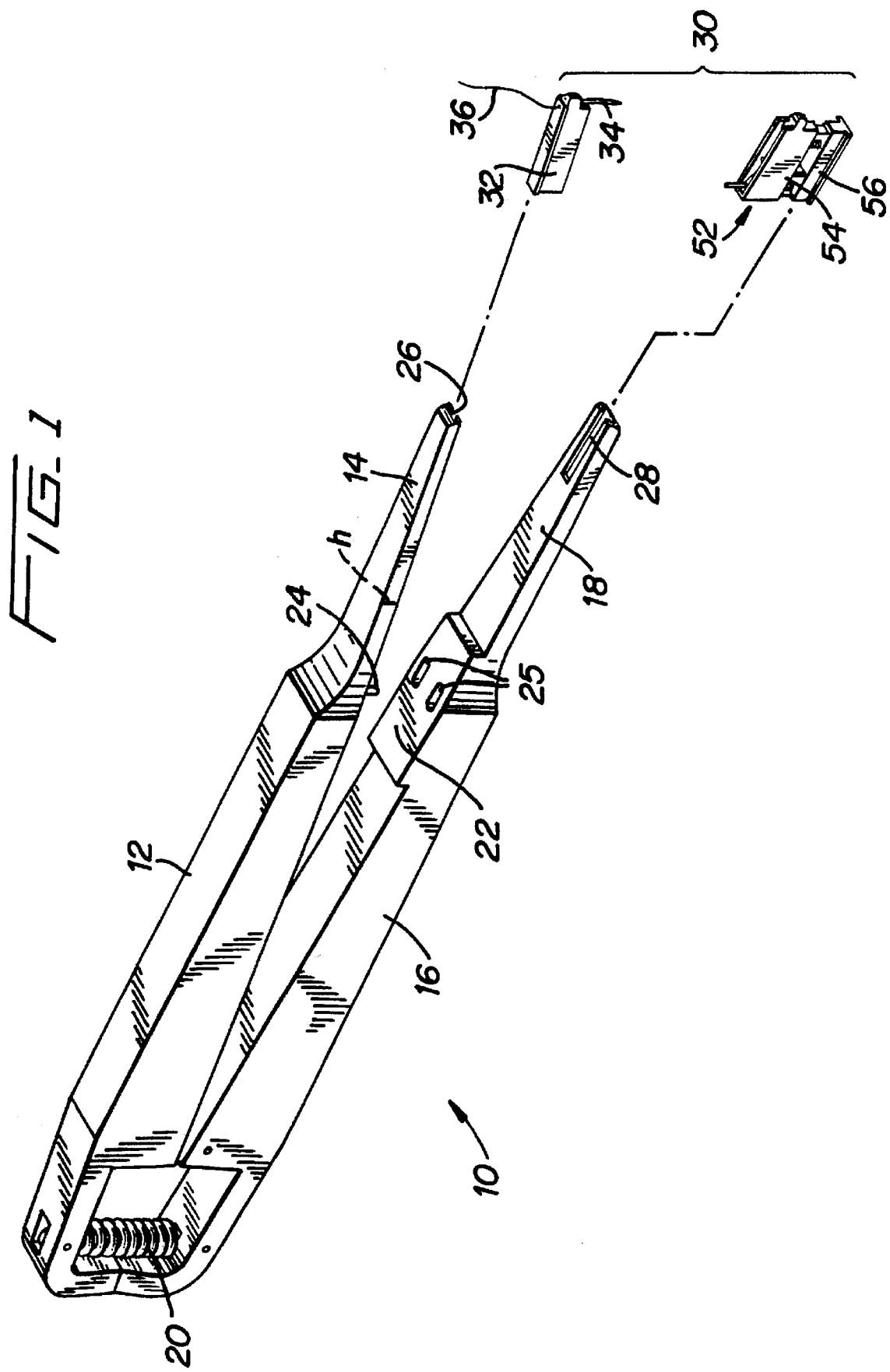

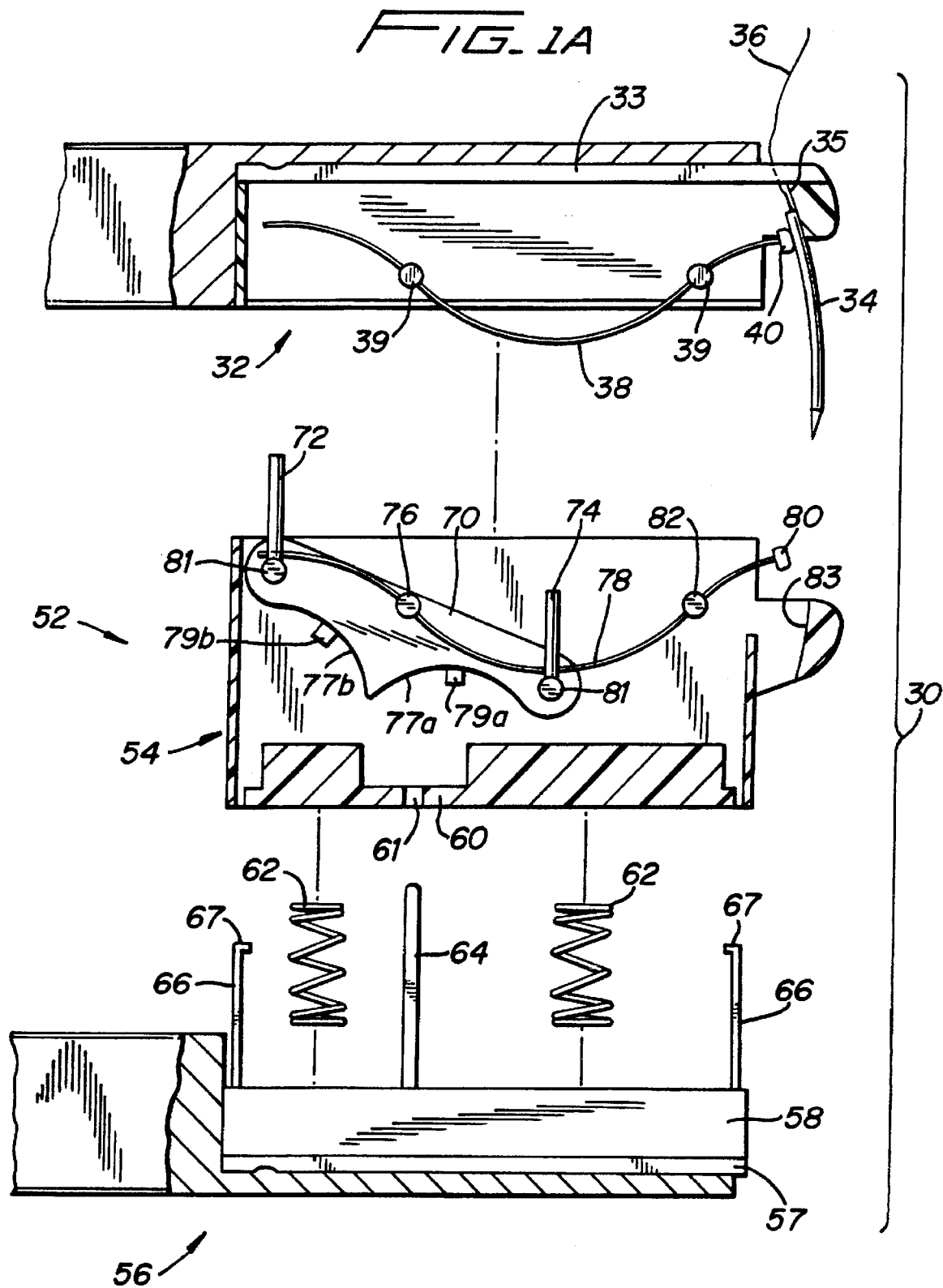

SURGICAL APPARATUS FOR SUTURING BODY TISSUE

BACKGROUND

1. Technical Field

The present application relates to an apparatus for suturing body tissue, and more particularly, to an apparatus which passes a surgical needle between its jaws and a disposable loading unit for loading a needle into the jaws.

2. Background of Related Art

During both open and minimally invasive (endoscopic) surgical procedures, suturing of body tissue can be time consuming for the surgeon. In endoscopic procedures, where surgery is performed in a body cavity and access to the site is through trocar cannulas, suturing is especially difficult. The surgeon cannot grasp the needle in his hand as in open surgery, but must rely on grasping instruments to grasp and maneuver the needle in the remote surgical site. These instruments entail grasping the surgical needle between the instrument jaws and manipulating the needle through the body tissue. Oftentimes, a second grasping instrument is required to enable passing the needle between the two instruments in the same manner the surgeon passes the needle between his hands during open procedures. Not only is maneuverability difficult, but the needle could slip from the jaws into the body cavity.

To this end, the instrument disclosed in EPO application 92308849.6 was developed. This instrument advantageously provided the surgeon with unprecedented control during suturing in endoscopic procedures. The surgical needle is passed between the jaws of the instrument and is retained in one of the jaws as they are opened. This instrument provided a marked advance over the earlier laparoscopic/endoscopic techniques of suturing. An improvement to the instrument disclosed in EPO Patent Application No. 92308849.6 is disclosed in U.S. patent application Ser. No. 08/134,145, filed Oct. 8, 1993, now abandoned. One of the advantages of this later instrument is it provided a disposable loading unit which enabled the needle and suture to be removed from the apparatus and reloaded with a fresh needle and suture.

The advantages attendant passing and retaining a surgical needle between instrument jaws is not limited to endoscopic applications. For example, in open vascular surgery, due to the extremely small size of the surgical needles, it is sometimes difficult for the surgeon to manipulate the needles between his/her hands. Additionally, the surgery is often done under magnification and the surgeon's repeated focus on the surgical site to pass the needle through the tissue, focus away from the surgical site to pass the needle between his hands in preparation for the next stitch, and then re-focus on the surgical site to continue stitching, is tiring and can cause eye strain. An instrument which passes the needle between the jaws overcomes these difficulties by allowing the surgeon to continuously focus on the surgical site during the entire vessel stitching procedure.

It would be advantageous to provide a suturing instrument which would enable a needle to be retained and passed between its jaws. It would further be advantageous to provide such an instrument that enabled quick and easy reloading of a fresh needle and suture, and could accommodate needles and sutures of various sizes/configurations and materials.

SUMMARY

A surgical apparatus for suturing body tissue is provided comprising first and second jaws relatively moveable between an open and closed position and first and second needle retaining sections removably mounted to the first and second jaws, respectively. A first securing mechanism is mounted in the first section and a second securing mechanism is mounted in the second section. A surgical needle is transferable between the first and second sections such that the surgical needle can be retained in either of the sections (and jaws) by the respective securing mechanisms. Each of the needle securing mechanisms preferably includes a spring movable between a clamping position to secure the surgical needle in the respective section and a release position to release the surgical needle from the section.

A toggle link is preferably provided for reciprocal movement between two positions to alternately move the first and second springs between the clamping and release positions. Each spring may include a clamping block for pressing the surgical needle against an inner wall of the respective section to secure it therein. A toggle finger may be mounted in the second section to contact and reciprocate the toggle link upon relative movement of the first and second jaws to the closed position. Preferably, movement of the first and second jaws to the closed position automatically pivots the toggle link from one of its positions to the other of its positions.

Also disclosed is a surgical needle loading unit for attachment to the surgical apparatus, wherein the loading unit has a first section having a first needle securing mechanism movable between a needle clamping position and a needle release position and a second section having a second needle securing mechanism movable between a needle clamping position and a release position. The first and second sections are detachably mounted to the first and second arms (jaws) of the apparatus, respectively. An actuator is positioned in one of the first and second sections for moving the first and second needle securing mechanisms between the clamping and release positions. A guide rail may be provided on each section of the loading unit for engagement with a slot formed in the respective arm of the apparatus. The actuator is preferably in the form of a toggle link mounted in the second section and engagable by an elongated toggle finger.

A kit may also be provided containing the apparatus and several disposable loading units, each loading unit containing a surgical needle and a mechanism for securing and transferring the needle between the instrument arms (jaws).

BRIEF DESCRIPTION OF THE DRAWINGS

Preferred embodiments of the surgical apparatus will be described hereinbelow with reference to the drawings wherein:

FIG. 1 is a perspective view of the apparatus showing the arms (jaws) in the open position and the disposable loading unit prior to being mounted to the arms;

FIG. 1A is an enlarged side cross-sectional view of the disposable loading unit;

FIG. 10A is a side view in partial cross section showing the proximal portion of the elongated shaft separated from the handle assembly;

FIG. 10B is a side view in partial cross section showing the elongated shaft mounted to the handle assembly;

FIG. 10C is an enlarged side cross-sectional view taken along lines 10c—10c of FIG. 10 showing the bayonet coupling of the elongated shaft.

DETAILED DESCRIPTION OF PREFERRED EMBODIMENTS

Figure 2:
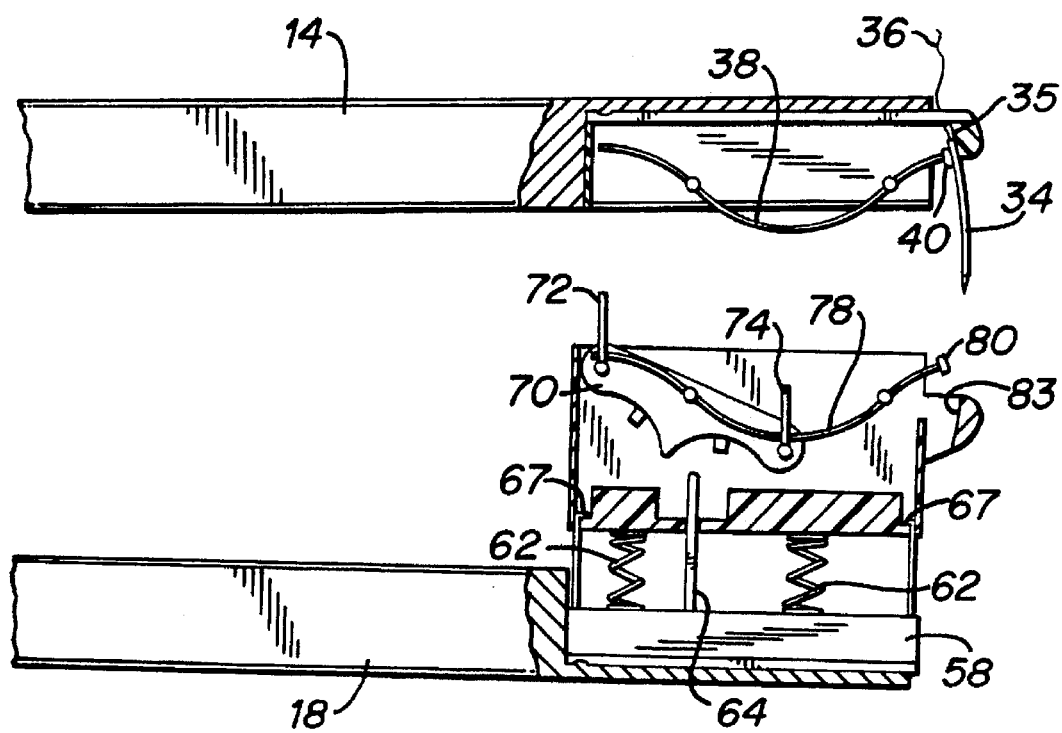
FIG. 2 is a side cross-sectional view illustrating a distal portion of the arms of the apparatus in the open position and the surgical needle retained in the upper arm.

Referring now to the drawings, and in particular to FIG. 1, both the apparatus 10 for suturing body tissue and the disposable loading unit 30 for loading a surgical needle into the apparatus are illustrated. The disposable loading unit 30 includes a surgical needle 34 with attached suture material 36 and a needle transferring mechanism which, when mounted to apparatus 10, enables the needle to be passed between the jaws of the instrument. The apparatus 10 achieves rapid suturing of body tissue and the provision of the loading unit enables the needles and sutures to be readily removed and replaced.

More specifically, apparatus 10 has upper and lower arms 12 and 16 connected at a proximal end and biased to an open position by spring 20. Arms 12 and 16 are configured to be grasped by the user and moved in a tweezer-like manner. Arm extensions or jaws 14 and 18 extend from upper and lower arms 12, 16, respectively, and are preferably tapered toward their distal ends and of reduced height h as compared to arms 12, 16 to improve access to the surgical site. A pair of spaced apart alignment pins 24, only one of which is shown, extend through the pair of openings 25 in the lower arm 16 to restrict lateral movement of the arms in the closed position. Raised stop block 22 limits the extent of movement of the jaws 14, 18 to the closed position.

It should be noted, that the terms "upper" and "lower" as used herein are for convenience and refer to the orientation of the apparatus shown throughout the figures. It should be appreciated that if the apparatus orientation changes, the o "upper" and "lower" designations will likewise change.

Turning now to the disposable loading unit, which is designated by reference numeral 30, the loading unit 30 includes an upper section 32 configured to be mounted to upper jaw 14 of upper arm 12 and a lower section 52 configured to be mounted to lower jaw 18 of lower arm 16. The loading unit 30 contains a surgical needle 34 and attached suture 36 and a mechanism for securing and releasing the needle 34. Although shown initially in upper section 32, the needle 34 could alternately be initially mounted in lower section 52. The loading unit provides for easy reloading of the instrument with a fresh needle and suture for continued use of the instrument during surgery, as well as enables different needles and sutures to be used with the apparatus 10. Thus, for example, the apparatus can be utilized for general surgery or for vascular surgery, e.g., to suture vessels, by providing a loading unit with an appropriately dimensioned needle. Additionally, if different types of sutures are required during a surgical procedure, e.g., absorbable and non-absorbable, the user can select the loading unit containing the desired suture and mount it to the apparatus in the manner described below.

The upper and lower sections 32, 52 are mounted to the apparatus via guide rails 33, 57. More specifically, with reference to FIGS. 1 and 1A, guide rail 33 is formed on the upper surface of section 32 and is dimensioned for engagement with an elongated dovetail slot 26 formed in upper arm 12. Similarly, guide rail 57 of section 52 is configured for engagement with elongated dovetail slot 28 of lower arm 16.

Figure 4:
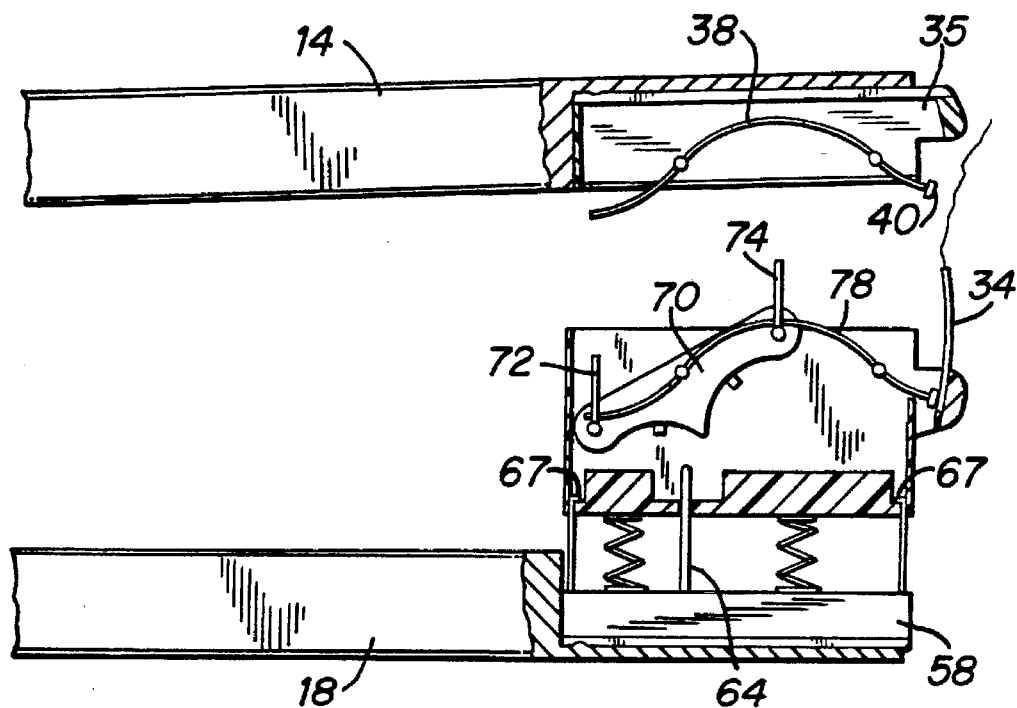
FIG. 4 is a side cross-sectional view showing the arms in the open position and the surgical needle retained in the lower arm.

Turning now to the first or upper section 32 of loading unit 30, with reference to FIGS. 1A and 2, the securing mechanism for securing (retaining) the surgical needle 34 in section 32 is in the form of leaf spring 38. Leaf spring 38 is mounted to upper section 32 by a pair of mounting pins 39 extending therethrough. A clamping block 40 is connected to the distal end of the spring 38 and presses the needle 34 against the inner wall 35 of section 32 when the spring 38 is in the clamping position. FIG. 2 illustrates the position of the clamping spring 38 when it is in the clamping (securing) position to secure the surgical needle 34 in section 32; FIG. 4 illustrates the position of clamping spring 38 when it is in the release position to release the surgical needle 34 from section 32. The actuator for moving spring 38 between these positions is described below.

With continued reference to FIGS. 1A and 2, the second or lower section 52 of loading unit 30 includes a base portion 56 and a toggle support portion 54 containing a needle securing mechanism and an actuating mechanism for manipulating the needle securing mechanisms positioned in the upper and lower sections 32, 52. An actuator finger 64 is positioned within base portion 56 and cooperates with the actuating mechanism of toggle support portion 54. As shown, the actuating mechanism is preferably in the form of a reciprocating toggle link 70 mounted to the toggle support portion 54 at its midpoint via pivot pin 76. Toggle link 70 is mounted and configured such that pivotal movement (rotation) a predetermined distance past its midline retains it in its rotated position. This over-center retaining feature of toggle link 70 enables the needle securing mechanisms to retain their position in the manner described below. A proximal spacer bar 72 and distal spacer bar 74, mounted via pins 81, extend upwardly from toggle link 70 and are configured to contact upper spring 38 of upper section 32 in a manner described in detail below. The securing mechanism for retaining the surgical needle 34 in toggle section 54 is preferably in the form of a leaf spring 78 similar in configuration to leaf spring 38 of upper section 32. Leaf spring 78 is mounted to the toggle link 70 by pivot pin 76, mounted to the body of the toggle portion 54 by retaining pin 82, and seated within a slot formed in each of the spacer bars 72 and 74. Both leaf springs 78 and 38 are configured so that they are self-retained in either the clamped or unclamped position.

Actuator toggle finger 64 is fixedly mounted to base 58 of base portion 56 and extends through an opening 61 in the floor 60 into toggle portion 54 for engagement with camming surfaces 77a, 77b (FIG. 1A) and camming blocks 79a, 79b of toggle link 70. Thus, the toggle finger 64 and toggle link 70 cooperate to actuate the needle securing mechanisms (springs 38, 78) of both upper and lower loading unit sections. A pair of compression springs 62 are positioned between base 58 and toggle support portion 54. Retaining walls 66 extend from base 58 and include a lip 67 which engages the floor 60 of the toggle portion 54 to retain the base portion 56 and toggle portion 54 together. Inner wall portion 83 cooperates with a clamping block 80 formed at the distal end of lower clamping spring 78 to securely retain the surgical needle 34 therebetween when spring 78 is moved to the clamping position. FIG. 4 illustrates the lower clamping spring 78 in the clamping (securing) position to secure surgical needle 34 in the lower section 52 and FIG. 2 illustrates the clamping spring 78 in the release position to release the surgical needle 34 from the lower section 52.

In use, if the disposable loading unit is not packaged attached to the apparatus, loading unit 30 is first mounted to the apparatus 10. Guide rail 33 of upper section 32 is slid into slot 26 of upper arm 14 to mount the section 32 to upper arm 12. Similarly, guide rail 57 of base portion 56 is slid into slot 28 to mount lower section 52 to lower arm 16. As shown in FIG. 1, the surgical needle 34 with attached suture 36, is initially positioned in the upper section 32. As noted above, alternatively, the surgical needle 34 can initially be secured in lower section 52. As shown in FIG. 2, surgical needle 34 is securely held in upper section 32 as it is clamped between clamping block 40 of upper clamping spring 38 and inner wall 35. In this initial position of FIG. 2, base portion 58 of lower section 52 is spaced from toggle support portion 54 so that flexible toggle finger 64 is out of contact with toggle link 70.

Figure 3:
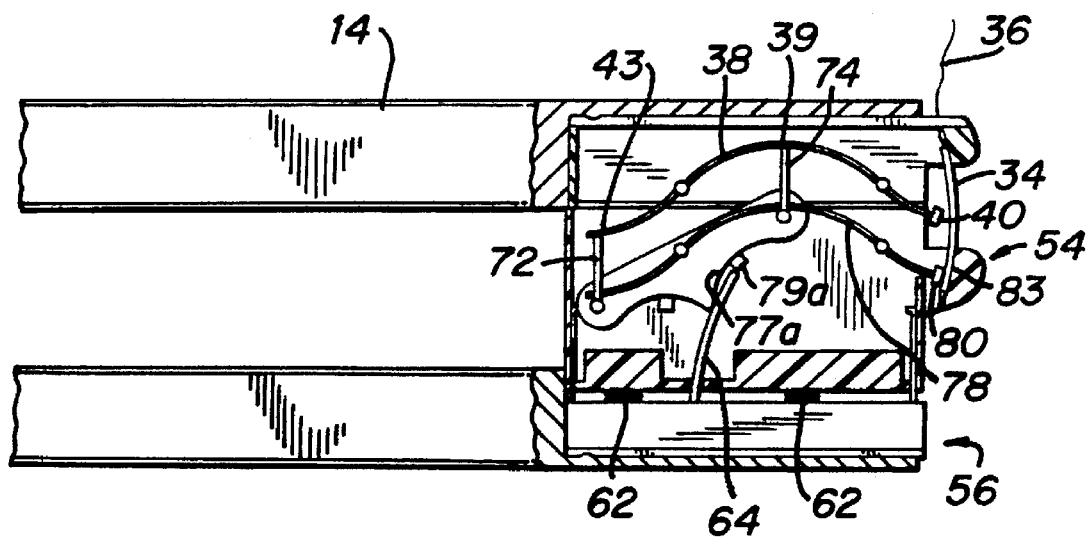
FIG. 3 is a side cross-sectional view showing the arms in the closed position and the toggle mechanism pivoted counterclockwise to release the surgical needle from the upper arm and secure it in the lower arm.

After placement of the instrument adjacent the body tissue to be sutured, finger applied pressure to upper and lower arms 12, 16 moves jaws 14, 18 to the closed position of FIG. 3. As the jaws are moved to the closed position, flexible toggle finger 64 travels towards toggle link 70 and springs 62 are compressed between base portion 56 and toggle support portion 54 of lower section 52. As base portion 58 and toggle support portion 54 are moved together, toggle finger 64 contacts and travels along camming surface 77a of toggle link 70 and engages camming block 79a to effectuate counterclockwise rotation of toggle link 70. As toggle link 70 is pivoted counterclockwise about pivot pin 76, distal spacer bar 74 contacts the buckled portion 39 of upper spring 38, forcing spring 38 to toggle to the position of FIG. 3. Furthermore, as toggle link 70 pivots counterclockwise, lower spring 78, carried by link 70 and spacer bars 72, 74 is toggled to the clamping position of FIG. 3. As a result, as shown in FIG. 3, the clamping block 40 of upper spring 38 is moved out of engagement with the surgical needle 34 to allow release thereof, while clamping block 80 of lower spring 78 is moved into abutment with surgical needle 34 and presses the needle against the inner wall 83 to securely retain the needle 34 in lower section 52. Thus, it can be appreciated that closing of the apparatus jaws automatically causes movement of the toggle link 70 counterclockwise to automatically pass the needle from securement in upper jaw 14 to securement in lower jaw 18.

When finger applied pressure on the upper and lower arms 12 and 16 is released to open jaws 14 and 18, as shown in FIG. 4, surgical needle 34 is securely held in lower section 52 and the toggle link 70, due to its over-center retaining feature described above, is retained in the counterclockwise rotational position shown.

Figure 5:
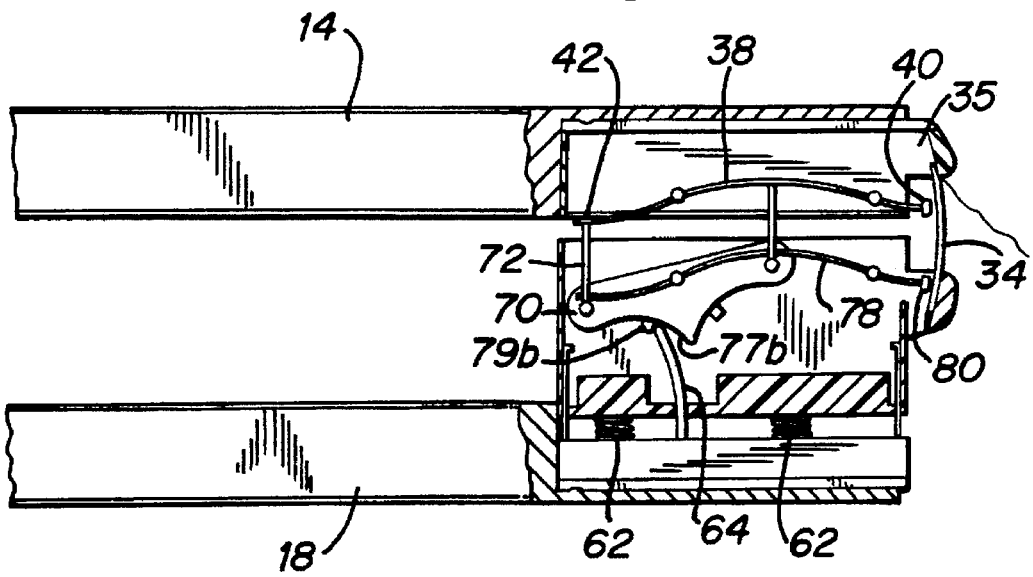
FIG. 5 is a side cross-sectional view showing movement of the arms towards the closed position and initial movement of the toggle mechanism clockwise to initiate transfer of the surgical needle from the upper arm to the lower arm.
Figure 6:
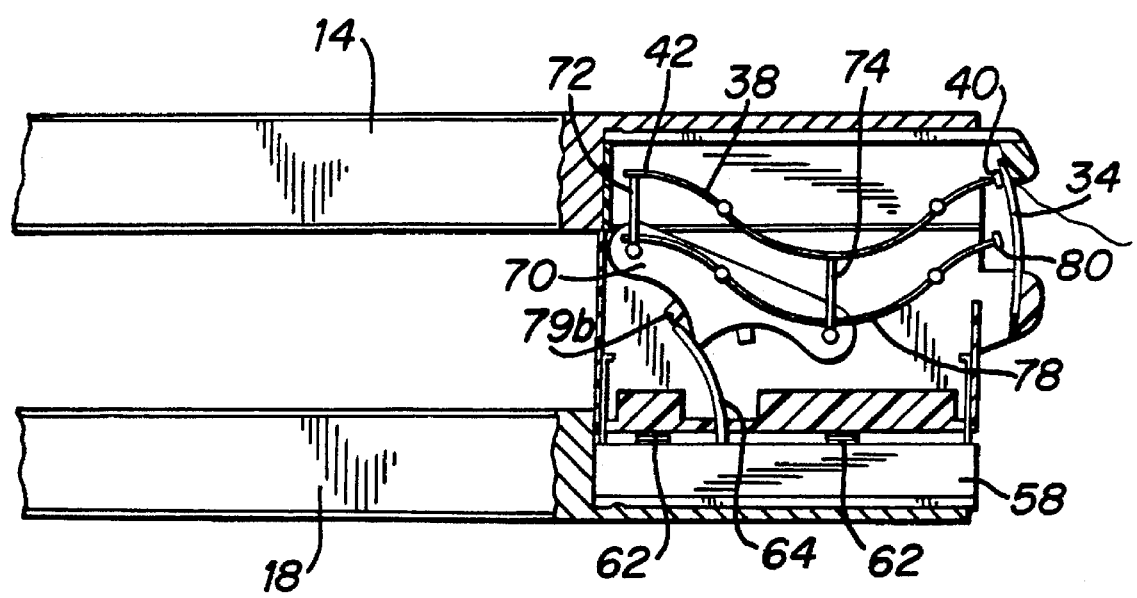
FIG. 6 is a side cross-sectional view illustrating the arms in the closed position and the toggle mechanism pivoted in a clockwise direction to release the surgical needle from the lower arm and secure it in the upper arm.

If the user desires to pass the surgical needle 34 back to the upper arm 12 (jaw 14) to continue suturing the body tissue, the arms 12 and 16 are once again squeezed together moving the jaws 14 and 18 to a closed position. As noted above, stop block 22 limits the closing movement of the jaws. As shown in FIGS. 5 and 6, as the jaws are closed, the toggle finger 64 contacts the toggle link 70 to initiate clockwise movement, sliding along camming surface 77b and engaging camming block 79b. As toggle link 70 is pivoted clockwise by the toggle finger 64, proximal spacer bar 72 contacts tail 42 of upper spring 38 forcing it to buckle and return to the position of FIG. 2. Additionally, as toggle link 70 pivots clockwise, it carries connected lower spring 78 to the position shown in FIG. 6. In this position of the springs 38, 78 of FIG. 6, clamping block 40 clamps surgical needle 34 against the inner wall 35 of upper section 32 to effectively secure the needle 34 in the upper section 32; and clamping block 80 of lower spring 78 is out of engagement with the surgical needle 34 to thereby release it from lower section 52. Thus, when the jaws are opened, the surgical needle 34 and the springs 38, 78, of upper and lower sections 32, 52 resume the position illustrated in FIG. 2.

To continue stitching, the user can repeatedly open and close arms 12 and 16 to successively pass the surgical needle 34 between the jaws 14, 18 in the manner described above. When the user has finished suturing at the surgical site, the upper and lower sections 32, 52 can be removed from the jaws 14 and 18 by sliding the respective guide rails 33, 57 out of the respective slots 26, 28 of jaws 14, 18. A new disposable loading unit, if desired, can then be mounted to the jaws 14, 18 in the manner described above.

As can be appreciated, closing of the jaws 14 and 18 automatically transfers the surgical needle 34 from the jaw in which it is retained to the opposing jaw. That is, the user does not need to actuate a separate mechanism for transferring the needle since closing of the jaws will automatically move the spring securing the needle to the release position and move the other spring to the clamping position.

Furthermore, the disposable loading unit 30 advantageously enables the needle to be easily loaded and unloaded from the instrument. This is particularly advantageous if the surgical apparatus is used in vascular procedures, e.g., for suturing vessels, since vascular needles are smaller in size and more difficult to handle. Additionally, the disposable loading unit 30 increases the versatility of the instrument. In a surgical procedure, it may be desirable to use needles of various sizes/configuration and sutures of various materials. Therefore, with the present apparatus, the surgeon can easily remove the disposable loading unit and replace it with another disposable loading unit having the desired surgical needle and suture material.

Although the disposable loading unit 30 described above contains two separate sections, each mounted to one of the arms (jaws) 14, 18 of the apparatus, it is also contemplated that a disposable loading unit can be provided which is mounted to only one of the arms. In such embodiment, one of the arms has a clamping spring and clamping block permanently mounted therein. The loading unit is mounted only to the other arm, wherein the loading unit contains the actuating mechanism and a clamping spring as described above, as well as the surgical needle. The needle is then passed between the jaws in the manner described above.

However, when it is desired to reload the instrument with another needle and suture, it is necessary to pass the needle to the loading unit and then remove the entire loading unit. In an alternate embodiment of a single section loading unit, i.e., mounted to only one arm, the actuating (toggle) mechanism and clamping spring are permanently positioned in one of the arms or jaws and the loading unit containing another clamping spring is removably mounted to the other arm. The needle is passed upon closing of the jaws as discussed above. In this embodiment, if the user wishes to reload the instrument, i.e., replace the needle and suture, the needle needs to be passed to the removable loading unit.

Figure 7:
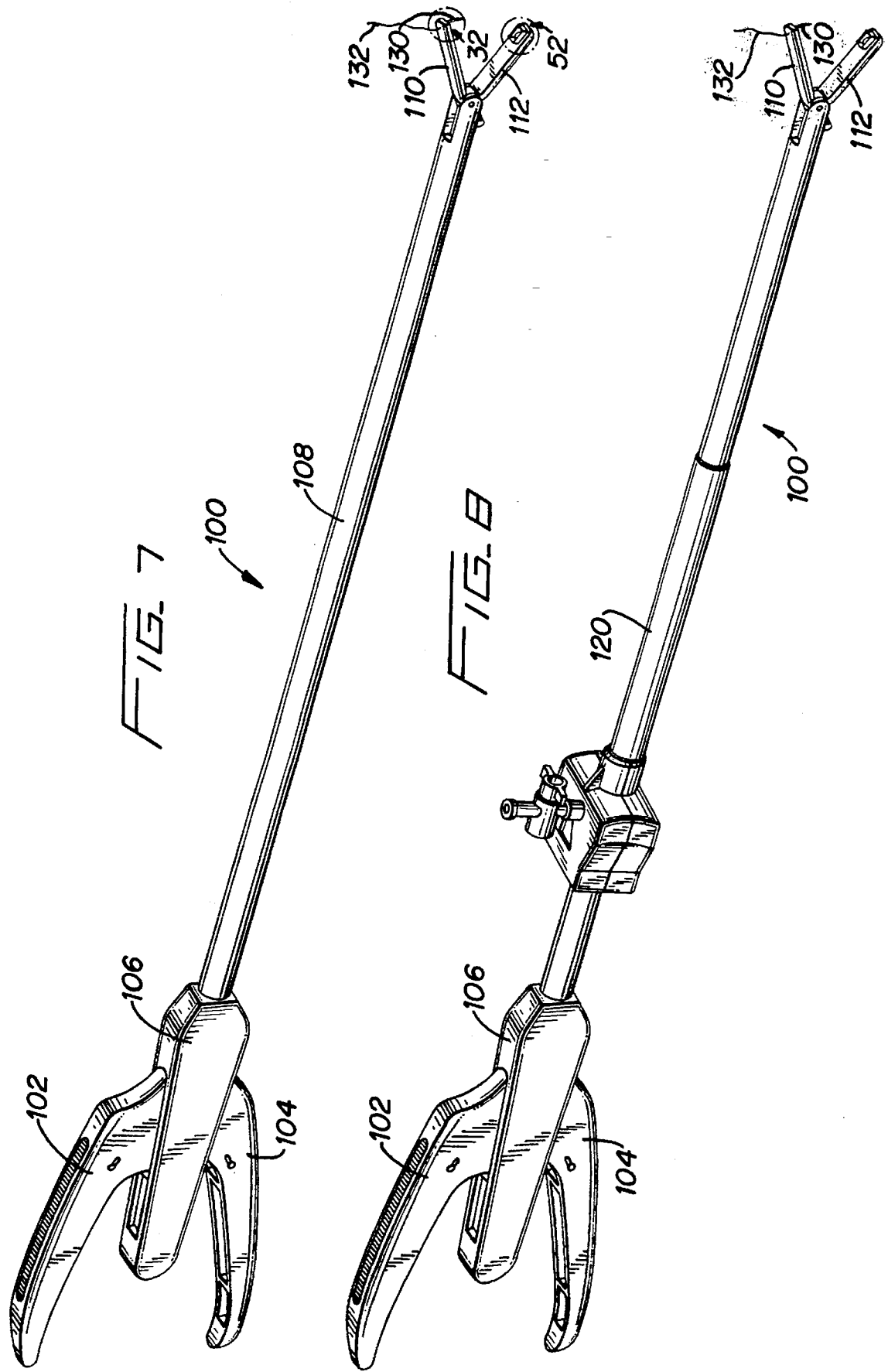
FIG. 7 is a perspective view of an alternate embodiment of the apparatus which is particularly adapted for endoscopic use, and showing the disposable loading unit mounted to the jaws.
Figure 8:
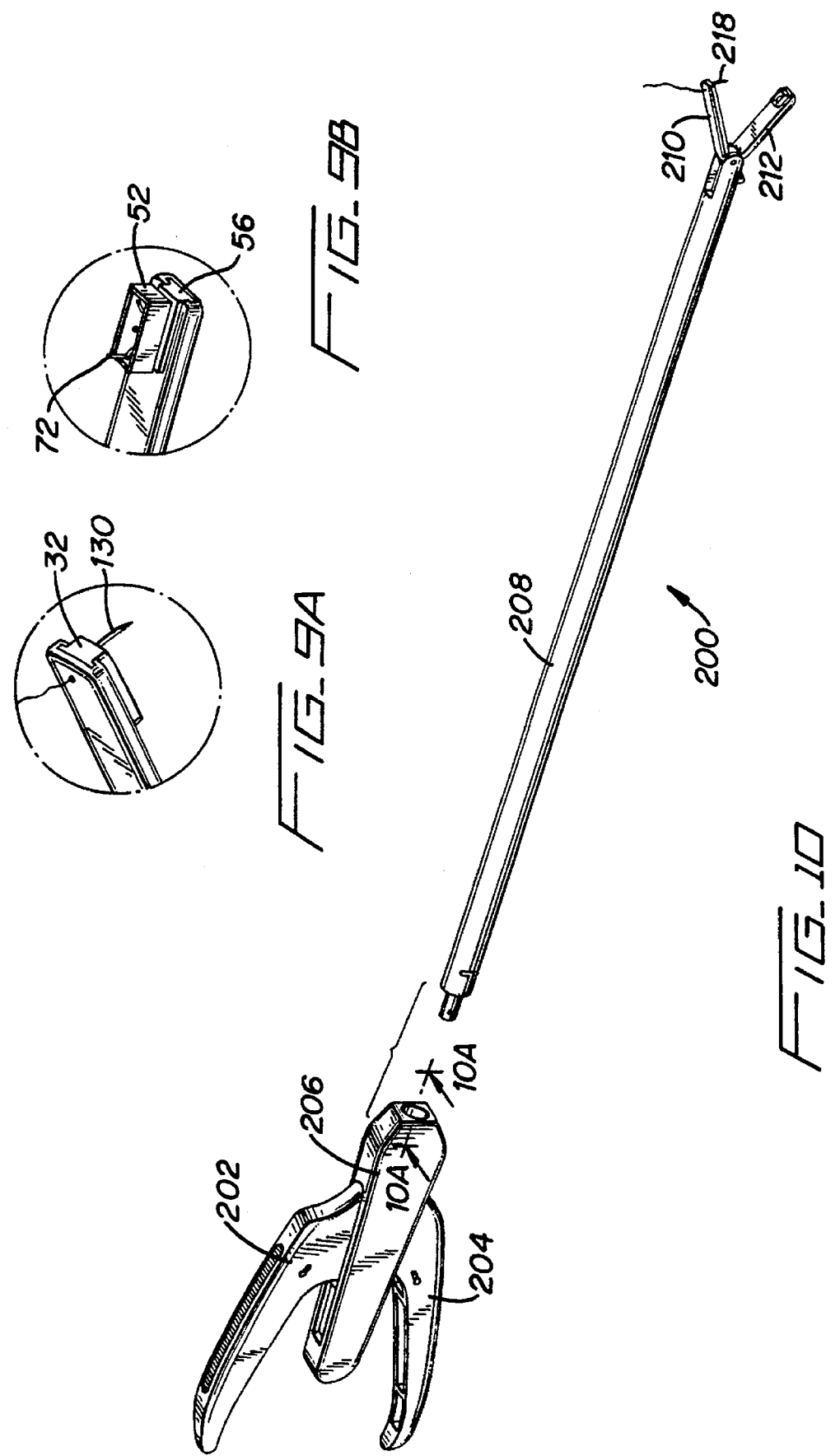
FIG. 8 is a perspective view of the apparatus of FIG. 7 inserted through a trocar cannula for use in endoscopic procedures.
Figure 9:
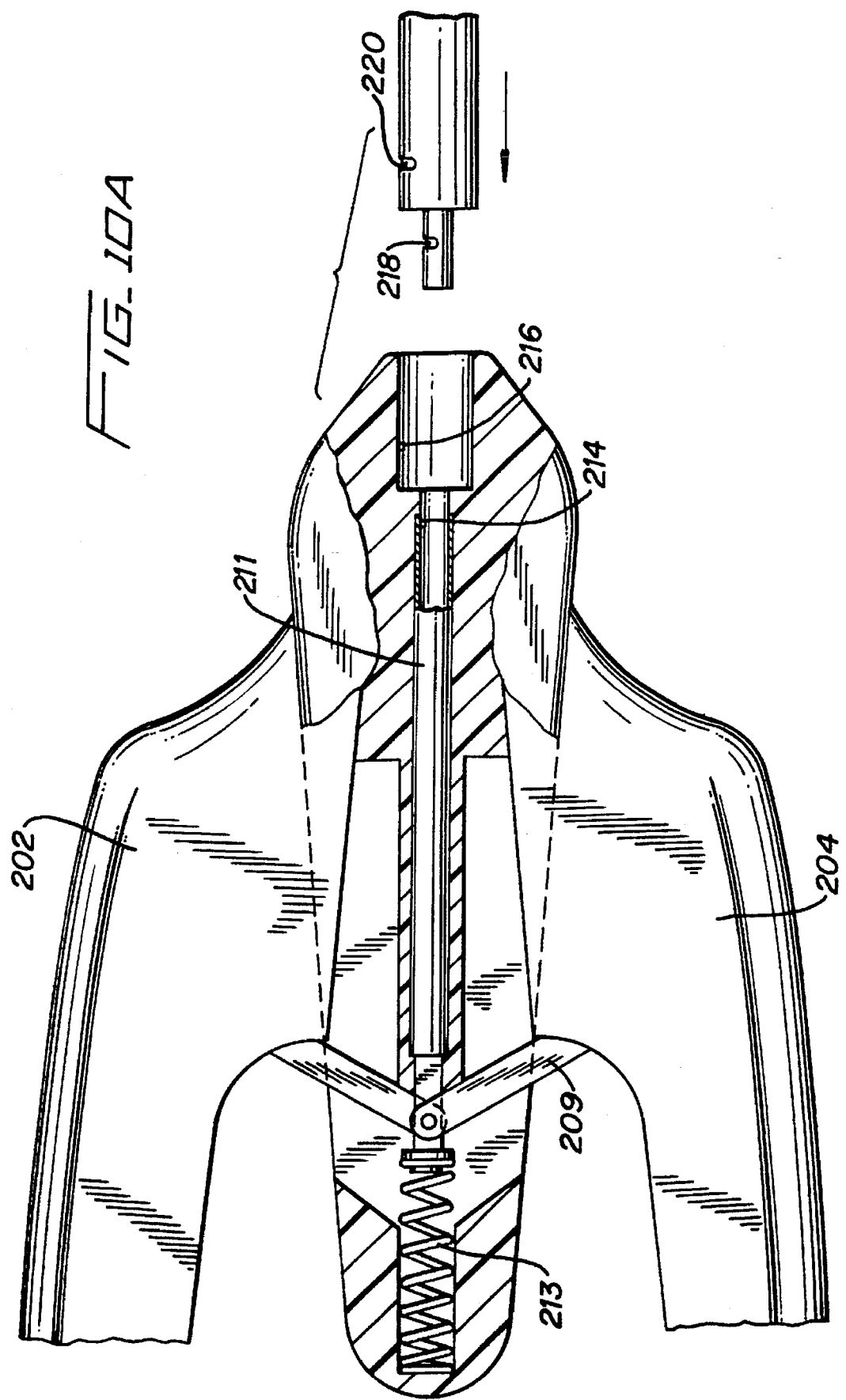
FIG. 9A is an enlarged perspective view showing the upper section of the disposable loading unit mounted to the upper jaw.
FIG. 9B is an enlarged perspective view showing the lower section of the disposable loading unit mounted to the lower jaw.

An alternate embodiment of the apparatus which is particularly adapted for endoscopic use is illustrated in FIGS. 7 and 8. Apparatus 100 has a handle assembly having a housing 106 and a pair of pivotably mounted handles 102 and 104, an elongated endoscopic tubular portion 108 extending from handle housing 106, and a pair of jaws 110, 112 pivotably mounted to a distal end of the tubular portion 108. Each of the jaws 110, 112 has an elongated slot substantially identical to the slots 26, 28 formed in the jaws 14 and 18 of FIG. 1 to receive the guide rails of the respective sections 32, 52 of the disposable loading unit. The disposable loading unit contains a first upper section 32 and a lower section 52 (see FIGS. 9A, 9B) identical in structure in structure to that described above. However, the dimensions of the components may differ depending on the size of the jaws 110, 112 compared to arms 14, 18.

In use of the endoscopic apparatus 100, the disposable loading unit is mounted to jaws 110 and 112 in the identical manner as that described above with respect to FIG. 1, the instrument is inserted through a trocar cannula 120 to access the remote surgical site in the body cavity, and handles 102, 104 are squeezed together to close the jaws 110, 112 and automatically transfer the needle between the jaws in the manner described above. The instrument can be withdrawn from the surgical site through the trocar and if desired, the disposable loading unit removed and the apparatus reloaded with a fresh needle and suture of the same or different configuration/material. It is also contemplated that the loading unit can be removed from the apparatus 100 and replaced with a fresh loading unit while the apparatus 100 is in the body cavity. A grasping instrument (not shown) can be inserted into the body cavity through another trocar site to grasp a portion of the loading unit and pull it out of engagement with the slot in the jaws. A fresh loading unit can likewise be inserted into the instrument while inside the body cavity using a grasping instrument.

Figure 10:
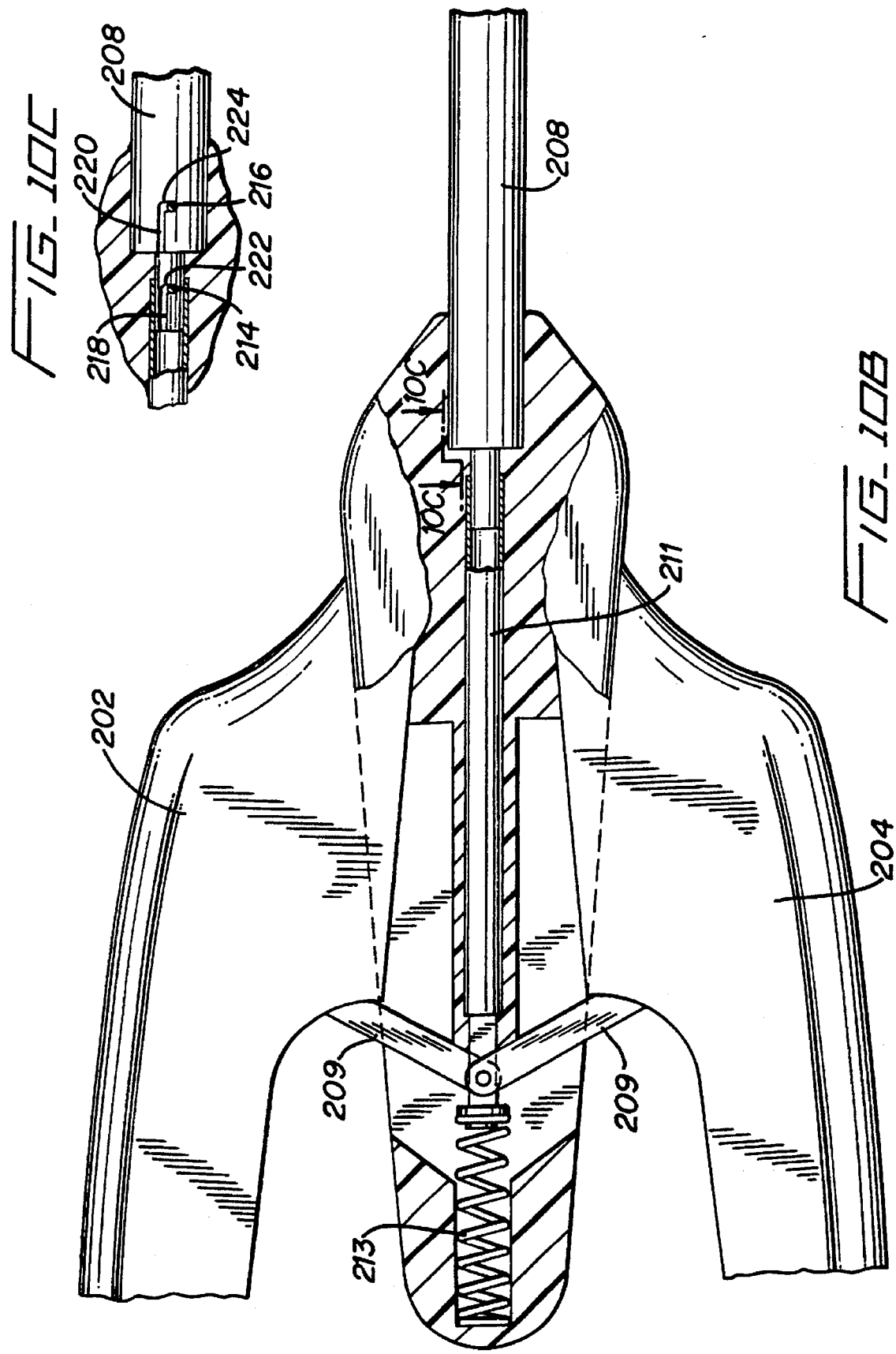
FIG. 10 is a perspective view of an alternate embodiment of an endoscopic apparatus illustrating the elongated shaft detached from the handle assembly.

An alternate embodiment of an endoscopic apparatus is shown in FIGS. 10A–10C, and is designated generally by reference numeral 200. Apparatus 200 also allows for the easy removal of the needle and reloading of a fresh needle and suture. However, in this embodiment, it is achieved in a different manner than in the embodiment of FIGS. 7 and 8 since instead of having a separate disposable loading unit removably attached to the jaws, the entire endoscopic shaft portion 208 is detachably mounted to handle housing 206.

As shown, shaft 208 is mounted to housing 206 via a bayonet coupling such that pins 214, 216 of housing 206 are inserted into slots 218, 220 in shaft 208, and rotated to be positioned in respective notches 222, 224 to secure the shaft 208 therein (see FIGS. 10B, 10C). The needle securing mechanisms, e.g. the flexible springs, and the toggle mechanism are identical to that described above with respect to FIGS. 1–8 except that the springs and toggle mechanisms are permanently mounted in the jaws. That is, instead of providing the disposable loading unit having removably mounted upper and lower sections, in this embodiment, one spring is non-removably mounted within one of the jaws 210 or 212 and another spring and toggle mechanism are non-removably mounted in the other jaw. Thus, when shaft 208 is mounted to handle housing 206 and handles 202 and 204 are squeezed together, links 209 pull actuator rod 211 proximally, overcoming the bias of spring 213, to cam jaws 210, 212 to the closed position. Movement of the jaws 210, 212 to the closed position automatically pivots the toggle link to transfer the surgical needle 218 between the jaws in the same manner as described above. After use, endoscopic shaft 208 (or housing 206) is rotated in the reverse direction to release the pins 214, 216 from the notches 222, 224, the shaft 208 is removed from the handle housing 206 and discarded, and a new shaft containing a fresh surgical needle and suture can be mounted to the housing 206.

Figure 11:
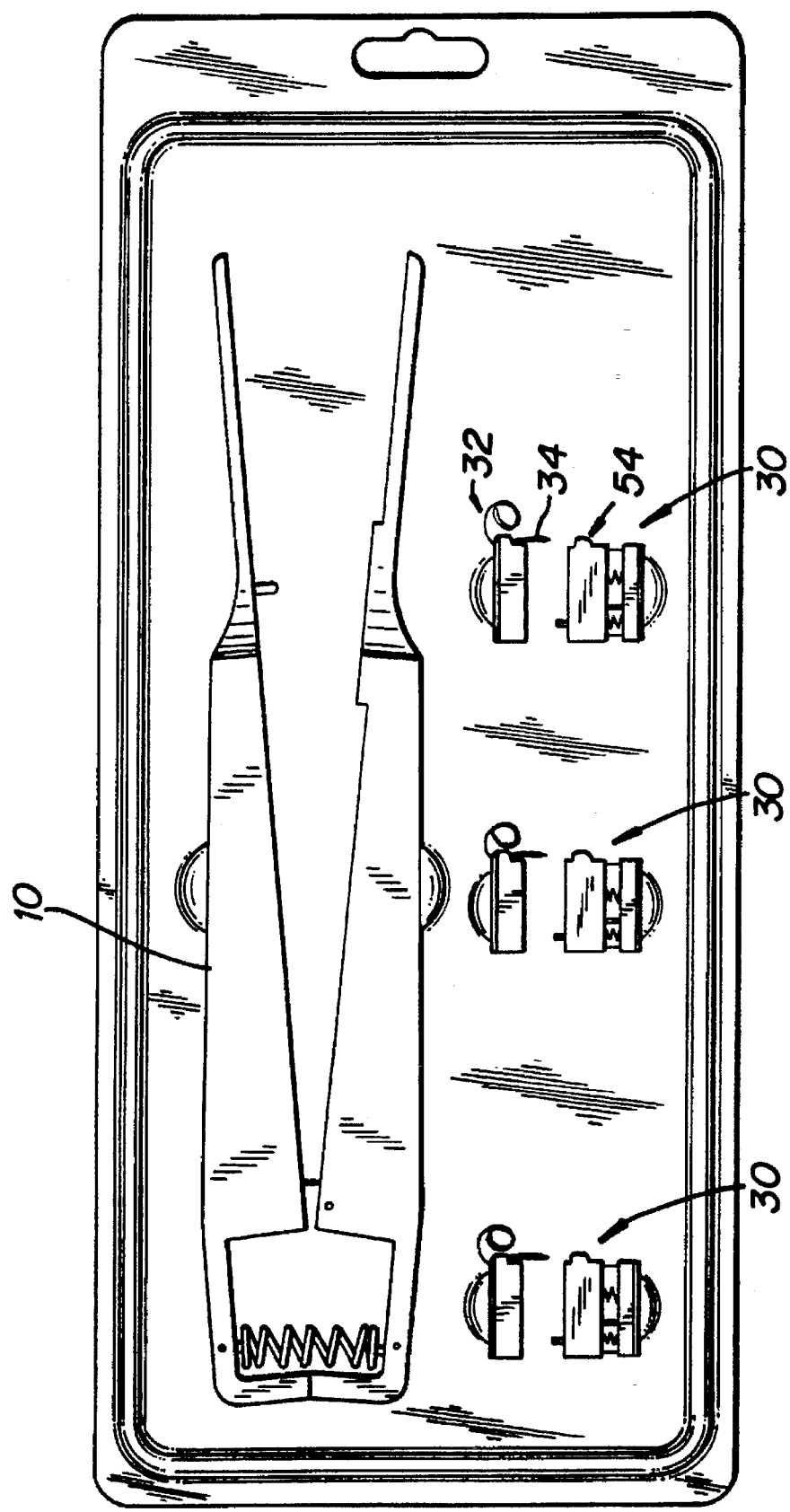
FIG. 11 is a top view of a kit containing the apparatus of FIG. 1 and three disposable loading units.

FIG. 11 illustrates a kit containing the sterile instrument 10 illustrated in FIG. 1 and three sterile disposable loading units 30. Although shown packaged with three disposable loading units, it is also contemplated that fewer or more loading units could be provided in the package and the loading units could contain needles and suture of the same or different configurations/materials. It is also contemplated that a package could include apparatus 100 of FIG. 7 containing several disposable loading units or the apparatus 200 of FIG. 11 containing a single handle housing 206 and several endoscopic shafts 208 with the same or different needle and suture configurations/materials.

It will be understood that various modifications may be made to the embodiments disclosed herein. For example, although the clamping spring is shown mounted to the sections by mounting pins, clearly other modes of securing the leaf springs can be utilized such as a detent in the spring engaging a slot formed in the body of the loading unit. Additionally, springs of different configurations are also contemplated. Therefore, the above description should not be construed as limiting, but merely as exemplifications of preferred embodiments. Those skilled in the art will envision other modifications within the scope and spirit of the claims appended hereto.

What is claimed is:

1. A surgical apparatus for suturing body tissue comprising:

first and second jaws, the first and second jaws being relatively movable between an open and closed position;

a first needle retaining section having a first securing mechanism mounted therein, the first section being removably mounted to the first jaw;

a surgical needle retained in the first needle retaining section by the first securing mechanism;

a second needle retaining section having a second securing mechanism mounted therein, the second section being removably mounted to the second jaw;

wherein the surgical needle is transferable between the first and second sections such that the surgical needle can be retained by the respective securing mechanism.

2. The apparatus of claim 1, wherein each of the securing mechanisms is movable between a clamping position to retain the surgical needle and a release position to release the surgical needle.

3. The apparatus of claim 2, further comprising a reciprocating member mounted in one of the first and second sections for reciprocal movement, the reciprocating member being engagable with both the first and second securing mechanisms to alternately move the first and second securing mechanisms between their clamping and release positions.

4. The apparatus of claim 1, wherein the first needle securing mechanism includes a first flexible spring movable between a clamping position to secure the surgical needle in the first section and a release position to release the surgical needle from the first section.

5. The apparatus of claim 4, wherein the second needle securing mechanism includes a second flexible spring movable between a clamping position to secure the surgical needle in the second section and a release position to release the surgical needle from the second section.

6. The apparatus of claim 1, wherein the first and second securing mechanisms each comprises a leaf spring, each of the leaf springs movable between a clamping position to secure the surgical needle in the respective needle retaining section and a release position to release the surgical needle from the respective needle retaining section.

7. The apparatus of claim 1, further comprising a handle mechanism and an elongated endoscopic portion positioned between the handle mechanism and the first and second jaws, wherein actuation of the handle mechanism closes the jaw.

8. A surgical apparatus for suturing body tissue comprising:

first and second jaws, the first and second jaws being relatively movable between an open and closed position;

a first needle retaining section having a first securing mechanism mounted therein, the first section being removably mounted to the first jaw;

a surgical needle retained in the first needle retaining section by the first securing mechanism;

a second needle retaining section having a second securing mechanism mounted therein, the second section being removably mounted to the second jaw;

the first needle securing mechanism including a first flexible spring movable between a clamping position to secure the surgical needle in the first section and a release position to release the surgical needle from the first section;

the second needle securing mechanism including a second flexible spring movable between a clamping position to secure the surgical needle in the second section and a release position to release the surgical needle from the second section; and a toggle link mounted in the second section for reciprocal movement to alternately move the first and second flexible springs between the clamping and release positions, wherein the surgical needle is transferable between the first and second sections such that the surgical needle can be retained by the respective securing mechanism.

9. The apparatus of claim 8, further comprising at least one elongated bar extending from the toggle link for contacting the first flexible spring to move the spring between the clamping and release positions.

10. The apparatus of claim 9, further comprising a clamping block positioned at a distal end portion of the first and second springs for pressing the surgical needle against an inner wall of the respective first and second sections.

11. The apparatus of claim 9, further comprising a toggle finger mounted in the second section, the toggle finger configured to contact and reciprocate the toggle link upon relative movement of the first and second jaws to the closed position.

12. A surgical apparatus for suturing body tissue comprising:

first and second jaws, the first and second jaws being relatively movable between an open and closed position;

a first needle retaining section having a first securing mechanism mounted therein, the first section being removably mounted to the first jaw;

a surgical needle retained in the first needle retaining section by the first securing mechanism;

a second needle retaining section having a second securing mechanism mounted therein, the second section being removably mounted to the second jaw;

the first and second securing mechanisms each comprising a leaf spring, each of the leaf springs movable between a clamping position to secure the surgical needle in the respective needle retaining section and a release position to release the surgical needle from the respective needle retaining section; and a reciprocating member movable between a first position and a second position, wherein movement of the reciprocating member to the first position moves the first leaf spring to the clamping position and the second leaf spring to the release position, and movement of the reciprocating member to the second position moves the leaf spring to the release position and the second leaf spring to the clamping position, wherein the surgical needle is transferable between the first and second sections such that the surgical needle can be retained by the respective securing mechanism.

13. The apparatus of claim 12, wherein the reciprocating member comprises a toggle link pivotably mounted in the second section.

14. The apparatus of claim 13, further comprising a toggle finger positioned in the second section and adapted to contact and pivot the toggle link between the first and second positions.

15. The apparatus of claim 14, wherein relative movement of the first and second jaws to the closed position automatically pivots the toggle link from one of the first and second positions to the other of the positions.

16. The apparatus of claim 15, further comprising a pair of camming blocks positioned on the toggle link to facilitate reciprocal movement thereof.

17. An apparatus for suturing body tissue comprising:

a first arm and a second arm the first arm movable between a first position spaced apart from the second arm and a second position adjacent the second arm;

a surgical needle loading unit mounted to at least the first arm, the loading unit including a surgical needle and a surgical needle retaining mechanism to secure the surgical needle in at least the first arm and to allow transfer of the surgical needle between the first and second arms, the needle loading unit including a first section removably attached to the first arm and a second section removably attached to the second arm, each of the first and second sections including a guide rail for mounting the respective first and second sections within a corresponding slot formed in the first and second arms, respectively, wherein the surgical needle loading unit is detachably connected to a distal portion of at least the first arm to allow removal and replacement of the loading unit.

18. The apparatus of claim 17, wherein the surgical needle retaining mechanism includes first and second springs mounted in the first and second sections, respectively, wherein each of the springs is movable between a clamping position to retain the surgical needle in the respective section and a release position to release of the surgical needle from the respective section.

19. The apparatus of claim 18, further comprising a toggle mechanism pivotally mounted in one of said first and second sections, the toggle mechanism moving the first and second springs between the clamping and release positions.

20. The apparatus of claim 19, wherein movement of the first and second arms to the closed position actuates the toggle mechanism to transfer the surgical needle between the first and second sections of the needle loading unit.

21. A surgical needle loading unit for attachment to a surgical apparatus having first and second arms for suturing body tissue, the loading unit comprising:

a first section having a first needle securing mechanism movable between a needle clamping position to retain the needle in the first section and a second position to release the needle from the first section, the first section being detachably mounted to the first arm;

a second section having a second needle securing mechanism movable between a needle clamping position to retain the needle in the second section and a release position to release the needle from the second section, the second section being detachably mounted to the second arm; and an actuator positioned in one of the first and second sections and operatively associated with the first and second needle securing members, the actuator alternately moving the first and second needle securing mechanisms between respective clamping and release positions.

22. The loading unit of claim 21, wherein the first and second sections each have a guide rail for engaging a slot in the first and second arms, respectively.

23. The loading unit of claim 21, wherein the actuator comprises a reciprocating member pivotably mounted within the second section.

24. The loading unit of claim 23, wherein the first securing mechanism comprises a first spring and the second securing mechanism comprises a second spring.

25. The loading unit of claim 24, wherein the reciprocating member is a toggle link having at least one elongated member for contacting the first spring to move it between the first and second positions.

26. The loading unit of claim 25, wherein the second spring is mounted to the toggle link.

27. The loading unit of claim 26, further comprising a toggle finger for reciprocating the toggle lever, the toggle finger contacting the toggle lever upon movement of the first and second arms of the apparatus to a closed position.

28. The loading unit of claim 27, wherein the toggle finger is biased out of contact with the toggle lever.

29. A surgical apparatus for suturing body tissue comprising:

a first jaw and a second jaw;

a first needle retaining section having a first needle securing mechanism mounted therein, the first section being removably mounted to the first jaw; and a second needle retaining section having a second needle securing mechanism mounted therein, the second section being fixedly mounted to the second jaw, wherein a surgical needle is transferrable from the first section to the second section and from the second section to the first section such that the surgical needle can be retained by the respective securing mechanism.

* * * * *